(12) United States Patent
Koenig et al.

(10) Patent No.: US 7,513,879 B2
(45) Date of Patent: Apr. 7, 2009

(54) NONINVASIVE ANGIOPLASTY USING MOMENTARY VACUUM THERAPY

(76) Inventors: J. Frank Koenig, 407 Kramer Dr., SE., Vienna, VA (US) 22180; John J. Basile, 3020 Hamaker Ct., Suite B-111, Fairfax, MD (US) 22031

( * ) Notice: Subject to any disclaimer, the term of this patent is extended or adjusted under 35 U.S.C. 154(b) by 36 days.

(21) Appl. No.: 11/415,420

(22) Filed: May 2, 2006

(65) Prior Publication Data

US 2007/0260110 A1    Nov. 8, 2007

Related U.S. Application Data

(63) Continuation of application No. 10/645,869, filed on Aug. 22, 2003, now Pat. No. 7,037,257.

(60) Provisional application No. 60/404,933, filed on Aug. 22, 2002.

(51) Int. Cl.
  *A61H 7/00*  (2006.01)
(52) U.S. Cl. ...................................................... 601/11
(58) Field of Classification Search .................. 600/20, 600/21, 38; 601/6–14
  See application file for complete search history.

(56) References Cited

U.S. PATENT DOCUMENTS

| | | | | |
|---|---|---|---|---|
| 2,134,646 | A | * | 10/1938 | Sauzedde ........................ 601/9 |
| 2,168,611 | A | * | 8/1939 | Thompson ...................... 601/9 |
| 3,465,748 | A | * | 9/1969 | Vasily ............................ 601/6 |
| 3,744,486 | A |   | 7/1973 | Wilson |
| 4,691,695 | A | * | 9/1987 | Birk et al. ....................... 601/6 |
| 4,718,411 | A |   | 1/1988 | Stewart |
| 4,738,249 | A | * | 4/1988 | Linman et al. ............... 601/152 |
| 5,897,512 | A | * | 4/1999 | Zagame .......................... 601/6 |
| 6,030,318 | A | * | 2/2000 | Howard .......................... 482/4 |
| 6,087,362 | A |   | 7/2000 | El-Rashidy |
| 6,183,414 | B1 |   | 2/2001 | Wysor et al. |
| 6,376,554 | B1 |   | 4/2002 | Cheetham et al. |
| 6,398,720 | B1 |   | 6/2002 | Dabal |
| 6,414,027 | B1 |   | 7/2002 | Neal |
| 6,436,944 | B1 |   | 8/2002 | Maytom |
| 6,455,564 | B1 |   | 9/2002 | Meglasson et al. |
| 6,482,426 | B1 |   | 11/2002 | Podolski |
| 6,548,544 | B1 |   | 4/2003 | Adaikan et al. |
| 6,589,990 | B1 |   | 7/2003 | Kanakaris et al. |
| 7,037,257 | B1 |   | 5/2006 | Koenig |

OTHER PUBLICATIONS

Marmar JL et al. The Use of a Vacuum Constrictor Device to Augment a Partial Erection Following an Intracavernous Injection, Nov. 1988, Journal of Urology, 140 (5) pp. 975-979.

Hubert John et al., Intraurethral Prostaglandin Improves Quality of Vacuum Erection Therapy, Dec. 1996, Karger, Uer Urol 1996; 29:224-226.

Massimo Cecchi et al., Vacuum constriction device and topical minoxidil for management of impotence, Arch. Esp. de Urol. 48, 10 (1.058-1.059) 1995.

Baniel et la., Comparative evaluation of treatment for erectile dysfunction in patients with prostate cancer after radical retropulic prostatectomy, BJU International, Jul. 2001 88, 58-62.

* cited by examiner

*Primary Examiner*—Samuel G Gilbert
(74) *Attorney, Agent, or Firm*—Shlesinger, Arkwright & Garvey LLP

(57) ABSTRACT

Noninvasive angioplasty using momentary vacuum therapy (MVT) is applied to treat erectile dysfunction, peripheral artery disease, and deep vein thrombosis. MVT is a noninvasive angioplasty technique which momentarily increases blood pressure to flatten arterial plaque and increase arterial elasticity for peripheral artery disease and deep vein thrombosis. The workload on the heart will be reduced by the flattening of plaque and the increase in elasticity of the peripheral arteries. The reduction in workload may be a treatment for congestive heart failure (heart failure). For treating erectile dysfunction, MVT increases the elasticity of penile arteries but does not flatten penile plaque; when treating erectile dysfunction with MVT, only an increase in arterial elasticity is required.

2 Claims, No Drawings ent application Ser. No. 10/645,869, filed Aug. 22, 2003, now U.S. Pat. No. 7,037, 257, Issued May 2, 2006, which claims the priority of 60/404, 933, filed Aug. 22, 2002, and each of which is incorporated herein by reference.

NONINVASIVE ANGIOPLASTY USING MOMENTARY VACUUM THERAPY

CROSS-REFERENCE TO RELATED APPLICATION

This application is a continuation of application Ser. No. 10/645,869, filed Aug. 22, 2003, now U.S. Pat. No. 7,037, 257, Issued May 2, 2006, which claims the priority of 60/404, 933, filed Aug. 22, 2002, and each of which is incorporated herein by reference.

CROSS-REFERENCE TO RELATED DISCLOSURE DOCUMENTS

This application relates to the following four (4) disclosure documents:
 1. Disclosure Document No. 510,869, filed May 6, 2002;
 2. Disclosure Document No. 507,608, filed Mar. 19, 2002;
 3. Disclosure Document No. 505,659, filed Feb. 20, 2002; and
 4. Disclosure Document No. 499,108, filed Aug. 29, 2001.

Copies of each of these four disclosure documents was attached to a filed with parent application Ser. No. 10/645, 869, filed Aug. 22, 2003, now U.S. Pat. No. 7,037,257, Issued May 2, 2006.

Retention of each of the above four disclosure documents was requested in that parent application Ser. No. 10/645,869, filed Aug. 22, 2003.

FIELD OF INVENTION

The present invention relates to noninvasive angioplasty using momentary vacuum therapy (MVT) which is used to treat erectile dysfunction, peripheral artery disease, and deep vein thrombosis. MVT is a noninvasive angioplasty technique which momentarily increases blood pressure to flatten arterial plaque and increase arterial elasticity for peripheral artery disease and deep vein thrombosis. For treating erectile dysfunction, MVT increases the elasticity of penile arteries but does not flatten penile plaque; when treating erectile dysfunction with MVT, only an increase in arterial elasticity is required.

BACKGROUND OF THE INVENTION

The National Institutes of Health estimates that 30 million American men suffer from mild, moderate or complete erectile dysfunction. Erectile dysfunction is the chronic (greater than three months duration) inability to maintain a penile erection sufficient to achieve penetration of one's sexual partner, complete sexual intercourse and/or achieve sexual satisfaction.

Most causes of erectile dysfunction have an adverse effect on nerves and/or blood vessels to, from, and within the penis.

Causes of erectile dysfunction include: atherosclerosis (thickening, narrowing, hardening and less elasticity of penile blood vessels); breakdown of a chemical message to or within the penis thereby preventing the erectile chambers from becoming engorged with blood to produce an erection; venous leakage (blood seeps out of the penile vessels instead of being trapped inside during an erection); nerve and blood vessel damage caused by diabetes; nerve damage caused by degenerative diseases such as multiple sclerosis and Parkinson's disease; nerve damage caused by surgical removal of prostate, bladder or rectum to treat cancer or other disease processes; abdominal aortic aneurysm (penile nerves and vessels may be damaged); B-12 deficiency (causes neurological problems throughout the body); radiation treatments for prostate, bladder and/or rectal cancer; psychological factors (stress, depression, performance anxiety); hormonal imbalances such as testosterone deficiency and/or abnormally high level of prolactin causing decreased libido (sexual desire); alcohol; tobacco usage; substance abuse; Peyronie's disease (penile connective tissue thickens thereby interfering with the ability to have an erection); injury to any nerves or arteries necessary to have an erection (pelvic fracture, brain, spinal cord, abdomen or penis); antihypertensives; antidepressants; tranquilizers; antifungals; antacids; cholesterol-lowering drugs; diuretics; nitrates; Proscar (medication for benign prostate hyperplasia); propecia (to counteract baldness); estrogens; antiandrogens; antihistimines; anticholinergics; anticancer drugs; aging, hypertension; obesity; hyper-cholesterolemia.

Known patents include:
U.S. Pat. No. 6,436,944 to Maytom.
U.S. Pat. No. 6,589,990 to Kanakaris et al.
U.S. Pat. No. 6,548,544 to Adaikan et al.
U.S. Pat. No. 6,414,027 to Neal.
U.S. Pat. No. 6,398,720 to Dabal.
U.S. Pat. No. 6,376,554 to Cheetham et al.

VIAGRA® (sildenafil citrate, Pfizer, Inc., New York, N.Y.), taken orally, is effective for up to 80% (depending upon the severity of erectile dysfunction (ED) and/or any underlying disease) of patients to produce an adequate erection for sexual intercourse. It is effective for a broad range of causes. Successful VIAGRA® patients have normal, natural erections. VIAGRA® has no effect on libido (sexual desire) so that it will not be effective unless a man feels stimulated.

When a man feels sexually stimulated, a chemical message in the penis causes the smooth muscle (lining the penile arteries) to relax so that these arteries dilate (widen) causing the two erectile chambers (corpora cavernosa) to become engorged with blood to produce an erection.

As a man ages, these chemical messages can be broken down by an enzyme in the penile tissues, causing erectile dysfunction. VIAGRA® prevents the breakdown of these chemical messages by suppressing the enzyme.

VIAGRA® suppresses the enzyme (phosphodiesterase) so that the erection-producing chemical cyclic guanosine monophosphate (cGMP) is not broken down so that a normal erection occurs.

cGMP is a natural vasodilator (dilates penile arteries) which relaxes the smooth muscle of penile arteries so that the relaxed smooth muscle, in combination with normal blood pressure, causes the penile arteries to dilate so that the erectile chambers are engorged with blood to produce an erection.

VIAGRA® is effective for 80% of men with psychogenic erectile dysfunction and about half of men whose erectile dysfunction is secondary to spinal cord injury, diabetes or radical prostatectomy.

VIAGRA® has no proven effect on penile atherosclerosis, a primary cause of erectile dysfunction. VIAGRA® may be ineffective when, e.g., the degree of atherosclerosis is too large so that, after sexual stimulation, the arteries are not sufficiently elastic so that the amount of arterial dilation is inadequate so that there is an insufficient amount of blood in the erectile chambers to produce an erection satisfactory for sexual intercourse.

VIAGRA® may have side effects including but not limited to: headache, flushing, upset stomach, nasal congestion, urinary tract infections, color tinge to vision, increased sensitivity to light, blurred vision, bloodshot or burning eyes, diarrhea, dizziness, rash, and, rarely, priapism (a painful, prolonged erection lasting more than four hours).

Men who cannot take VIAGRA® or find it ineffective are often able to achieve erections by using another treatment which produces erections directly, without sexual stimulation. This treatment uses vasodilation (vessel dilation) by means of medications (vasodilators) which dilate the penile arteries so that the erectile chambers become engorged with blood to produce an erection. These medications relax the smooth muscle of penile arteries to cause arterial dilation.

The most common vasodilator is ALPROSTADIL® (Caverjet, Edex, Schwarz Pharma USA Holdings, Inc., Wilmington, Del.). It can be injected into the base of the penis (into one of the corpora cavernosa) with a needle or inserted into the urethra in pellet form through a delivery system calls MUSE (Medicated Urethral Suppository for Erection). ALPROSTADIL® is effective in over 80% of patients and MUSE for about 30% of men with erectile dysfunction. For men for whom ALPROSTADIL® is ineffective, an injected mixture of vasodilators (TRIMIX) is effective for about 62% of patients.

The side effects of injected ALPROSTADIL® are penile pain, bruising, scarring, priapism (a painful, prolonged erection) and decreased blood pressure. The side effects of MUSE are urethral burning, dizziness and decreased blood pressure. The effective lowest dose minimizes side effects for injections and MUSE.

Since vasodilators cause erections directly, without sexual stimulation, by dilating penile arteries, they may be effective, such as when the penile neurovascular bundles are no longer intact; e.g., when VIAGRA® is ineffective.

A non-invasive treatment for erectile dysfunction is the hand-held vacuum pump (Vacuum Erection Device, Osbon Medical Systems). A plastic cylinder (connected to the pump) is placed over the penis and a partial vacuum is quickly achieved, after pumping several times, which draws blood into the penis thereby dilating the vessels to achieve an artificial erection. A rubber constricting ring is placed temporarily at the base of the penis to prevent blood from escaping from the penis. The constricting ring may remain in place for not more than thirty minutes or damage to the penis may result.

Men who are able to achieve a normal erection but cannot sustain it because they have venous leakage may be helped by a penile constriction band. This is a ring-like device that is fastened around the base of the penis to keep blood from escaping. A penile band called Actis is available (Vivus Corp.).

When other therapies are ineffective, surgical implants may be considered. One device consists of two silicone rods implanted in the penis. The penis is permanently erect and can be pointed down along the thigh or up toward the abdomen to conceal it under clothing.

Another type of implant consists of two inflatable cylinders put into the corpora cavernosa which produce an erection when filled with saline fluid. The fluid is pumped from a reservoir implanted in the space of retzius and then fluid is transferred to the penile cylinders when an erection is desired.

A new medication Uprima (apomorphine), taken orally, is under study. It seeks to target mechanisms in the brain to produce an erection. It has been approved in Europe for treatment of erectile dysfunction.

A topical medication Topiglan (ALPROSTADIL®), under study, has had promising results, applied to the head of the penis to produce an erection directly, without sexual stimulation. An ointment would ease the mode of delivery while reducing the risk of adverse effects compared to injection or urethral pellet.

Two oral medications, awaiting FDA approval, are vardenafil and tadalafil. They, like sildenafil (VIAGRA®) are PDE-5 inhibitors which suppress the enzyme which breaks down the natural vasodilator cGMP in order to facilitate and maintain an erection.

When two or more medications are used in combination, the treatment is called combination pharmacotherapy. When a medication is used alone, the treatment is called monotherapy. When any monotherapy fails, a combination pharmacotherapy may be effective.

Combination pharmacotherapies using at least two medications have been used experimentally with significant results. The combination of VIAGRA® and MUSE has been evaluated (Eur. Urol. 2000; 38: 30-4 and BJU. Int. 2000; 86: 469-73 and Urol. 2000; 163: 198).

Another study evaluated the benefit of oral alpha blockers (daily oral doxazosin) in combination with intracavernosal (injected) ALPROSTADIL® (Urol. 1998; 52: 739-43).

Another study (Internat. J. Impot. Res. 2002; 14(1): 50-53) combines VIAGRA® with daily oral Cardura (doxazosin).

Two ALPROSTADIL® studies are described in Prostate Disorders, The Johns Hopkins White Papers, 2002, p. 57. Scientists hypothesized that regular (periodic) injections of vasodilators, independent of sexual activity, might help bring about the return of normal, natural erections. In a small 12-week study, 67% of radical prostatectomy patients regularly injected with ALPROSTADIL® eventually achieved normal, natural erections, compared to 20% of those who did not receive injections. Other results were also reported in a one year study (Urology, 2001; 57 (3)), not cited in the White Papers.

A study set forth in the above-described Johns Hopkins White papers of 270 radical prostatectomy patients regularly (periodically) receiving MUSE (ALPROSTADIL® by urethral pellet), independent of sexual activity, showed that this treatment may be successful in achieving normal, natural erections in 40% of cases.

OBJECTS AND SUMMARY OF THE INVENTION

An object of the present invention is to provide a treatment for erectile dysfunction comprising momentary vacuum therapy, used alone, for patients for whom atherosclerosis is the primary cause of erectile dysfunction.

Another object of the present invention is to provide a treatment for erectile dysfunction, for patients for whom an erectile dysfunction medication, including a PDE-5 inhibitor, such as VIAGRA® has never been effective, comprising momentary vacuum therapy with VIAGRA®.

Another object of the present invention is to provide a treatment for erectile dysfunction, for patients for whom VIAGRA® was effective but has become less effective or ineffective, comprising momentary vacuum therapy with VIAGRA®.

Another object of the present invention is to provide a treatment for erectile dysfunction, for patients who cannot use an adequate dose of VIAGRA® to produce a satisfactory erection due to adverse side effects, comprising momentary vacuum therapy with a reduced dosage of VIAGRA®.

Another object of the present invention is to provide a treatment for erectile dysfunction, for those patients for whom ALPROSTADIL® has never been effective in producing an adequate erection, comprising momentary vacuum therapy with ALPROSTADIL®.

Another object of the present invention is to provide a treatment for erectile dysfunction, for patients for whom ALPROSTADIL® was effective but has become less effective or ineffective, comprising momentary vacuum therapy with ALPROSTADIL®.

Another object of the present invention is to provide a treatment for erectile dysfunction, for patients who cannot use an adequate dose of ALPROSTADIL® to produce a satisfactory erection due to adverse side effects, comprising momentary vacuum therapy with a reduced dosage of ALPROSTADIL®.

Another object of the present invention is to provide a treatment for erectile dysfunction, for patients for whom a combination pharmacotherapy has been ineffective, comprising momentary vacuum therapy with the combination pharmacotherapy.

Another object of the present invention is to provide a treatment for erectile dysfunction, for patients for whom a combination pharmacotherapy was effective but has become less effective or ineffective, comprising momentary vacuum therapy with the combination pharmacotherapy.

Another object of the present invention is to provide a treatment for erectile dysfunction, for patients who cannot use an adequate dose of a combination pharmacotherapy to produce a satisfactory erection due to adverse side effects, comprising momentary vacuum therapy with a reduced dosage of the combination pharmacotherapy.

Another object of the present invention is to provide a treatment for erectile dysfunction when regular (periodic) use of ALPROSTADIL®, independent of sexual activity, is ineffective for eventually producing normal, natural erections. The treatment comprises the regular (periodic) use of momentary vacuum therapy with ALPROSTADIL® which may eventually produce normal, natural erections.

Another object of the present invention is to provide an effective treatment for erectile dysfunction comprising regular (periodic) momentary vacuum therapy, used alone, independent of sexual activity, so that normal, natural erections may eventually occur.

Another object of the present invention is to provide a treatment to enhance (increase) erectile firmness for successful VIAGRA® patients, by means of a treatment comprising momentary vacuum therapy with VIAGRA®.

Another object of the present invention is to provide a treatment to enhance (increase) the erectile firmness of successful ALPROSTADIL® patients, by means of a treatment comprising momentary vacuum therapy with ALPROSTADIL®.

Another object of the present invention is to provide a treatment for each successful VIAGRA® patient, currently using the minimum effective dosage, who wants to reduce the dosage below minimum and continue to be successful. The treatment comprises momentary vacuum therapy with a reduced dosage of VIAGRA®, below the minimum effective dosage.

Another object of the present invention is to provide a treatment for each successful ALPROSTADIL® patient, currently using the minimum effective dosage, who wants to reduce the dosage below minimum monotherapy dosage and continue to be successful. The treatment comprises momentary vacuum therapy with a reduced dosage of ALPROSTADIL®, below the minimum effective dosage for the patient.

DESCRIPTION OF THE INVENTION

For many years urologists have prescribed a non-invasive treatment for erectile dysfunction which produces an artificial erection. The patient used a hand-held vacuum pump attached to a plastic cylinder (to create a partial vacuum) to draw blood into the penile vessels and dilate the vessels to produce a very firm penis. While the vessels are dilated, a rubber constricting ring is placed at the base of the penis to prevent blood from leaving the penis so that an artificial erection occurs. The performance of penile nerves is not altered by the constricting ring in that known treatment.

All treatments of the present invention use the hand-held manual or battery operated vacuum pump (with cylinder), alone or with medications. The constricting ring is not used. For all treatments the cylinder is pumped momentarily (several times) to produce a very firm penis. Then the patient presses the stop button so that room air enters the cylinder and the penis becomes flaccid. Then the pump and cylinder are removed.

In the present invention the momentary use of the pump to momentarily produce a very firm penis is called vacuum therapy (momentary vacuum therapy).

Consider a patient who suffers from erectile dysfunction because, after sexual stimulation, the penile arteries do not dilate sufficiently so that the erectile chambers do not become engorged with blood to produce an erection satisfactory for sexual intercourse.

This patient may be helped by a treatment of the present invention comprising the administration of momentary vacuum therapy, used alone, immediately prior to sexual stimulation. Immediately after vacuum therapy the penis becomes flaccid. Then, after sexual stimulation, a natural erection may be achieved satisfactory for sexual intercourse.

After treatment and sexual stimulation, the penile arteries dilate to a sufficient, increased amount, compared to no treatment, so that the patient achieves a successful erection.

For this patient, without treatment and after sexual stimulation, the natural vasodilator cGMP relaxes arterial smooth muscle but the arterial dilation is insufficient to produce a satisfactory erection. After treatment and sexual stimulation a satisfactory erection may be produced.

This suggests that vacuum therapy, which momentarily dilates the arteries, has increased the arterial elasticity so that, after sexual stimulation, cGMP relaxes the arterial smooth muscle and normal blood pressure is able to dilate the arteries to a sufficient, increased extent so that the patient may have an erection satisfactory for sexual intercourse. In other words, with increased elasticity, due to vacuum therapy, the arteries are less rigid (less inelastic) so that they provide less opposition to dilation so that normal blood pressure dilates the arteries an increased amount, compared to no treatment, so that a normal erection may be produced satisfactory for sexual intercourse. Vacuum therapy, by increasing arterial elasticity, overcomes arterial rigidity caused by atherosclerosis. This treatment may be effective when atherosclerosis is the primary cause of erectile dysfunction and other causes are not significant.

This treatment was found to be effective, in practice.

All treatments of the present invention use the finding of the present invention that momentary vacuum therapy increases the elasticity of arteries.

Compared to vacuum therapy, used alone, it was found that the treatments of the present invention comprising momentary vacuum therapy with VIAGRA® are required by an increasing number of patients because they require that the atherosclerosis problem and the chemical message problem be treated simultaneously in order to achieve a normal, natural erection.

For all treatments of the present invention for which VIAGRA® is prescribed, any other medication of this class of PDE-5 inhibitors which performs the same function may be substituted for VIAGRA®.

For safety, the pump is designed so that penile blood pressure will not exceed a safe upper limit corresponding to a safe maximum vessel dilation. The pump can produce a momentary maximum safe amount of arterial dilation, which is greater than the maximum amount achievable with a vasodilator medication.

Another treatment of the present invention may be effective for patients for whom the maximum permissible dosage of VIAGRA® has never been effective. The treatment comprises momentary vacuum therapy with VIAGRA®. Successful patients achieve a natural erection after sexual stimulation. In this case the atherosclerosis problem and the chemical message problem are treated simultaneously. As shown later, in many cases the increased arterial elasticity, due to vacuum therapy, has the effect of reducing the required VIAGRA® dosage to achieve a satisfactory erection. The preferable time to use the momentary pump is immediately prior to sexual stimulation.

This treatment was found to be effective in practice.

EXAMPLES

Example 1

A sixty-four year old male subject (patient) diagnosed with erectile dysfunction, was treated with VIAGRA® up to the maximum clinically recommended dosage of 100 mg. The maximum dosage was ineffective. Momentary vacuum therapy was then prescribed in combination with the administration of a clinically recommended dosage of VIAGRA®. At a 50 mg dosage level, in combination with momentary vacuum therapy applied to the patient's penis prior to intercourse, the treatment was effective so that an erection suitable for sexual intercourse was achieved. The achievement of the satisfactory erection was apparently caused by increased arterial elasticity thanks to the administration of momentary vacuum therapy.

Another treatment of the present invention may be effective for VIAGRA® patients for whom the maximum dosage of VIAGRA® has become less effective or ineffective. The treatment comprises momentary vacuum therapy with VIAGRA®. The preferable time to use the pump is immediately prior to sexual stimulation. This treatment was found to be effective before or after the VIAGRA® patient becomes erectile dysfunctional. In many cases the VIAGRA® dosage may be reduced when VIAGRA® is used with vacuum therapy, thus precluding the onset of adverse VIAGRA®-related side effects in some patients.

This treatment was found to be effective in practice.

Example 2

A male subject, sixty-eight years old, diagnosed with erectile dysfunction, had been treated effectively for two (2) years, at the maximum clinically recommended dosage of 100 mg of VIAGRA®. Over time, the efficacy of the maximum recommended dosage gradually lessened and failed to achieve an erection satisfactory for intercourse. Vacuum therapy was then prescribed in combination with the 100 mg dosage of VIAGRA®. This combination therapy was effective in restoring erectile function, apparently because arterial elasticity had been increased due to the momentary vacuum therapy, thus resulting in increased penile arterial dilation, and an erection satisfactory for intercourse. A reduced VIAGRA® dosage is effective in many cases because the increased arterial elasticity (due to vacuum therapy), in combination with a smaller quantity of the natural vasodilator cGMP (facilitated by the reduced VIAGRA® dosage), provides a sufficient increase in arterial dilation causing the erectile chambers to become engorged with blood to produce an erection satisfactory for sexual intercourse.

In penile vacuum therapy the hand-held vacuum pump, producing momentarily increased penile blood pressure, dilates all penile vessels simultaneously without the need for an invasive procedure. In contrast, balloon coronary angioplasty, an invasive procedure, is applied to one location at a time in each coronary artery.

Another treatment of the present invention is applicable to patients who have adverse side effects from VIAGRA® treatment at the minimum VIAGRA® dosage necessary to produce an adequate erection. Many of these patients will not attempt VIAGRA® usage again because of the resultant VIAGRA®-induced adverse side effect(s) produced at this minimum effective dose.

It was found that many of these patients benefit from a treatment of the present invention comprising vacuum therapy and a reduced dosage of VIAGRA®. By enabling patients with erectile dysfunction to lower the VIAGRA® dosage, some adverse side effects can be avoided or sufficiently reduced in many patients. Although this reduced dosage of VIAGRA®, if used alone, will be inadequate to produce an erection, the combined usage of the vacuum pump and this reduced VIAGRA® dose may be effective in producing a satisfactory erection in many of these patients who otherwise would continue to suffer from erectile dysfunction.

This treatment was found to be effective, in practice.

Example 3

A male subject, forty-seven years old, had been diagnosed with erectile dysfunction. An initial prescribed dosage of 50 mg of VIAGRA® was ineffective in achieving an erection satisfactory for intercourse. A maximum clinically recommended dosage of 100 mg of VIAGRA® was then prescribed and found to be effective; however, the subject experienced headaches at the 100 mg maximum dosage, the headaches being too severe for patient comfort. There had been no side effects reported by the patient at the 50 mg VIAGRA® level. Momentary vacuum therapy was then prescribed to the subject in combination with VIAGRA® at the 50 mg dosage level; i.e., a combination therapy. The subject was then able to achieve an erection satisfactory for intercourse without side effects (e.g., headaches) under this combination therapy regimen.

Another treatment of the present invention may be effective for patients for whom ALPROSTADIL® has never been effective. Effectiveness may be achieved by means of a treatment of the present invention comprising momentary vacuum therapy with ALPROSTADIL®. Vacuum therapy is used immediately prior to the administration of ALPROSTADIL® (penile injection or urethral pellet) or other injectable medications which perform the same function as ALPROSTADIL®

ALPROSTADIL® relaxes the arterial smooth muscle to cause arterial dilation and the pump provides increased arterial elasticity. The arterial dilation may be sufficient enough such that the erectile chambers become engorged with enough blood to produce a satisfactory erection.

When using a typical dosage of ALPROSTADIL®, used alone, the amount of arterial dilation will be insufficient if the patient has significant penile atherosclerosis, so that a satisfactory erection may not occur due to an inadequate degree of arterial elasticity.

In treatments of the present invention, one or more vasodilators (used alone or in combination with other vasodilators) may be substituted for ALPROSTADIL®.

Another treatment of the present invention may be effective for ALPROSTADIL® patients for whom the maximum dosage of ALPROSTADIL® has become less effective or ineffective due to disease, e.g., increased atherosclerosis. The treatment comprises momentary vacuum therapy with ALPROSTADIL®. The patient uses the pump immediately prior to the administration of ALPROSTADIL®. This treatment may be effective before or after the ALPROSTADIL® patient becomes erectile dysfunctional.

In many cases the ALPROSTADIL® dosage may be reduced because vacuum therapy increases arterial elasticity and ALPROSTADIL® relaxes smooth muscle of penile arteries, so that the reduced dosage of ALPROSTADIL®, with vacuum therapy, may produce increased arterial dilation, compared to ALPROSTADIL®, used alone, so that the erectile chambers may become engorged with sufficient blood to produce an erection suitable for sexual intercourse.

The vacuum pump has been used within 5-20 minutes after penile injection therapy to facilitate erections, in accordance with the invention.

Another treatment of the present invention may be effective for patients who have adverse side effects from ALPROSTADIL®, so that they avoid the use of this medication. Many of these patients benefit from a treatment of the present invention comprising momentary vacuum therapy and a reduced dosage of ALPROSTADIL® because often the dosage of ALPROSTADIL® can be reduced when using momentary vacuum therapy, thereby reducing or eliminating adverse side effects. This allows many patients to achieve satisfactory sexual intercourse who otherwise would continue to suffer from erectile dysfunction. The hand-held vacuum pump should be used momentarily immediately prior to the administration of ALPROSTADIL® or 5-20 minutes after penile injection therapy.

Adequate erections may be achieved by a treatment according to the present invention comprising regular (periodic) momentary vacuum therapy, used alone, independent of sexual activity, described later.

Another treatment of the present invention may be effective for patients for whom regular (periodic) administration of ALPROSTADIL® (injection or urethral pellet), independent of sexual activity, does not eventually lead to normal, natural erections after treatment is discontinued. Effectiveness may be achieved by a treatment of the present invention comprising the regular (periodic) administration of momentary vacuum therapy with ALPROSTADIL® which may eventually achieve normal, natural erections.

Periodic vacuum therapy with ALPROSTADIL® gradually increases arterial elasticity to a greater degree than can be achieved by periodic ALPROSTADIL®, used alone, thereby overcoming the reduced elasticity of arteries, caused by atherosclerosis, so that successful patients achieve normal erections. Patients who have a significant chemical message problem will not be successful.

Another treatment of the present invention comprises regular (periodic) application of momentary vacuum therapy, used alone, independent of sexual activity, which may eventually lead to normal, natural erections.

The periodic application of vacuum therapy produces a gradual increase in arterial elasticity, over time, so that normal erections may eventually be achieved. The treatment may be effective for penile atherosclerosis patients provided that other causes of erectile dysfunction are not significant.

Another treatment of the present invention may enhance (increase) the penile erectile firmness of successful VIAGRA® patients, by means of a treatment comprising momentary vacuum therapy with VIAGRA®.

For successful VIAGRA® patients, enhanced erectile firmness may be achieved with the VIAGRA®-vacuum therapy treatment provided that this treatment achieves increased arterial dilation, compared to VIAGRA® alone, resulting in a larger quantity of blood in the erectile chambers, providing an enhanced erectile firmness. This will result in increased patient satisfaction.

Another treatment of the present invention may enhance (increase) the penile erectile firmness of successful ALPROSTADIL® (used alone) patients, by means of a treatment comprising momentary vacuum therapy with ALPROSTADIL®. For successful ALPROSTADIL® (used alone) patients, enhanced erectile firmness may be achieved with the ALPROSTADIL®-vacuum therapy treatment provided that this treatment achieves increased arterial dilation, compared to ALPROSTADIL® alone, resulting in a larger quantity of blood in the erectile chambers, providing an enhanced erectile firmness. This will result in increased patient satisfaction.

Another treatment of the present invention may be effective for each successful VIAGRA® patient, currently using the minimum effective dosage, who wants to reduce the dosage below minimum and continue to be successful. The treatment comprises momentary vacuum therapy with a reduced dosage of VIAGRA®, below the minimum effective dosage. The patient will have a satisfactory erection when combining the reduced VIAGRA® dose, which by itself would not produce an adequate erection, with vacuum therapy if the arterial dilation after sexual stimulation is sufficient so that the erectile chambers become engorged with blood to produce an erection satisfactory for sexual intercourse. Vacuum therapy is applied immediately prior to sexual stimulation.

Another treatment of the present invention may be effective for each successful ALPROSTADIL® patient, currently using the minimum effective dosage, who wants to reduce the dosage below minimum and continue to be successful. The treatment comprises momentary vacuum therapy with a reduced dosage of ALPROSTADIL®, below the minimum effective dosage.

The patient will have a satisfactory erection when combining the reduced ALPROSTADIL® dose, which by itself would not produce an adequate erection, with vacuum therapy if the arterial dilation after sexual stimulation is sufficient so that the erectile chambers become engorged with sufficient blood to produce an erection satisfactory for sexual intercourse. Vacuum therapy is applied immediately prior to sexual stimulation.

In treatments of the present invention, combination pharmacotherapies may be substituted for VIAGRA® or ALPROSTADIL®. When a monotherapy (e.g., VIAGRA® or ALPROSTADIL®) treatment fails, a combination pharmacotherapy (e.g., VIAGRA® and ALPROSTADIL®) may be effective. When a monotherapy or a combination pharmacotherapy fails, then success may be achieved by a treatment of the present invention comprising momentary vacuum therapy with the monotherapy or combination pharmacotherapy.

Noninvasive Angioplasty Using Momentary Vacuum Therapy

Momentary vacuum therapy not only increases penile arterial elasticity but may also flatten arterial plaque by means of increased blood pressure on the arterial walls so that there is a larger arterial opening for blood flow.

Bulb angioplasty is effective, e.g., for coronary and thigh arteries. Momentary vacuum therapy may be useful if applied to the whole leg or whole arm or to a portion of arm or leg. For example, if a whole leg is enclosed by a cylinder attached to a vacuum pump, momentary vacuum therapy can increase the blood pressure to be the same as the arterial pressure applied by the bulb so that all leg arteries are treated simultaneously, which may increase arterial elasticity and also flatten plaque throughout the leg by means of this noninvasive treatment.

Congestive heart failure (heart failure) patients may benefit from momentary vacuum therapy applied to arms and/or legs because heart workload is reduced by this treatment. After treatment there may be increased blood flow throughout the body.

When momentary vacuum therapy (MVT) is applied to arms and legs, the flattening of arterial plaque will open arteries so that the workload of the heart will be reduced.

Heart workload reduction will aid in the treatment of congestive heart failure (also called heart failure). Heart failure patients have a weakened pump (i.e., heart) as compared to patients having a normal heart.

In order to apply MVT to a thigh, alone, it is necessary to apply a tourniquet immediately above or below the knee to prevent blood from being drawn into the thigh from the lower leg when the thigh is subjected to MVT. That is, it is necessary to apply a tourniquet at a distal part of the thigh. When MVT is applied to an encased thigh, blood will be drawn from the trunk of the body into the thigh arteries to momentarily increase blood pressure to flatten plaque and to increase arterial elasticity.

Instead of using a laboratory test procedure to determine whether a man has penile atherosclerosis, alternative diagnostic methods, such as differential diagnosis, are as described in Cases I and II discussed below. If one used a laboratory test procedure and found atherosclerosis, one would not know how to relate the laboratory finding to erectile dysfunction, as a man can be functional, even given some degree of penile atherosclerosis. In Cases I and II it is shown how to treat the male patient having erectile dysfunction given the simple inventive treatments with which treatments the efficacy and effectiveness is readily apparent.

Case I

When a man has erectile dysfunction, momentary vacuum therapy (MVT), alone, may be prescribed to determine what will solve the problem; i.e., treat the erectile dysfunction. In such a case, only a small percentage of men will become erectile functional; i.e., will regain erectile function. For those who remain dysfunctional after using MVT, a PDE-5 inhibitor (e.g., VIAGRA®) may be prescribed in combination with MVT. If this combination therapy is effective, it may be concluded that the PDE-5 inhibitor caused a sufficient amount of the natural vasodilator cGMP to be available to the patient so as to relax the patient's arterial smooth muscle in the penis, and that (2) the inventive momentary vacuum therapy increased the arterial elasticity of atherosclerotic arteries.

Administration of a PDE-5 inhibitor and administration of the inventive momentary vacuum therapy may be administered independent of each other, as each performs its own independent physiological function.

Case II

When a man has erectile dysfunction, a PDE-5 inhibitor (e.g., VIAGRA®), used alone, is effective in a large percentage of cases. If the maximum safe dosage of the PDE-5 inhibitor is ineffective, then momentary vacuum therapy may be prescribed in combination with the PDE-5 inhibitor. If this combination is effective, then we conclude that the PDE-5 inhibitor did its job and momentary vacuum therapy did its job, independent of each other.

The inventors of the present invention made the medical finding that dilation of atherosclerotic arteries will increase elasticity of arteries. This finding has been extremely important in the treatments in accordance with the present invention. All of the treatments of the present invention use MVT, alone, or in combination with medication. As described herein, only a minority of men require only MVT alone to be successfully treated for erectile dysfunction.

Hand Vacuum Pump With Constriction Ring

The pump with ring has been known for a long time. When the pump is used to obtain a firm penis, suitable for sexual intercourse, it is known that the constriction ring should be used to prevent blood from leaking from the penis into the trunk of the body in order to maintain a firm penis, suitable for sexual intercourse for 30 minutes.

It is well known that if the ring is not used, the penile firmness will rapidly become unsatisfactory to the patient, owing to venous leakage.

The inventive momentary vacuum therapy is a simple, effective procedure which aids the user to obtain a normal, natural erection. In most cases, the MVT is used with medications to obtain a normal, natural erection.

Deep Vein Thrombosis

When momentary vacuum therapy is applied to the thigh, lower leg and foot, arterial plaque may be flattened and arterial elasticity may be increased. Blood flow will be increased as the arteries are more open.

There will be increased blood flow in these thigh, lower leg, and foot arteries as well as in the veins which return blood to the heart. The increased blood flow in the veins may reduce the risk of deep vein thrombosis.

In erectile dysfunction treatments one does not need flattening of penile arterial plaque. In surgical work, no penile arterial plaque flattening has been found.

Concerning flattening of plaque with MVT, we have found that penile arterial plaque is not flattened by MVT. Elasticity is increased. It is believed the reason why no flattening has been found is because the penile arteries are not held in place by muscle as in heart and thigh and lower leg arteries. For thigh and lower leg arteries, when MVT is applied to an artery, a muscle restrains arterial dilation so that the increasing blood pressure of MVT will flatten plaque. The strength of the arterial wall also has a restraining effect on arterial dilation.

While this invention has been described as comprising a number of treatments, it is understood that it is capable of further modifications, uses and/or adaptations of the invention following in general the principle of the invention and including such departures from the present disclosure as come within the known or customary practice in the art to which the invention pertains and as may be applied to the central features hereinbefore set forth, and fall within the scope of the invention and of the limits of the appended claims.

What is claimed is:

1. A method for treating a body part of a human diagnosed with arterial atherosclerosis to achieve one of increased arterial elasticity and a flattening of arterial plaque within the body part, the method comprising:
   a) selecting a human subject having arterial atherosclerosis in a body part, the body part being a thigh;
   b) administering momentary vacuum therapy to the thigh of the human subject, the administering of momentary vacuum therapy to the thigh being administered a sufficiently long period of time to achieve one of increased arterial elasticity and a flattening of arterial plaque within the thigh; and
   c) the method being performed with the use of a tourniquet on a distal part of the thigh of the human subject on which the momentary vacuum therapy is being administered, and the method being performed with noninvasive angioplasty.

2. The method of claim 1, wherein:
   a) the distal part of the thigh is one of above and below the knee.

* * * * *